United States Patent [19]
Brown

[11] Patent Number: 5,591,171
[45] Date of Patent: Jan. 7, 1997

[54] ADAPTER AND METHOD FOR MEASURING PRESSURES OF FLUID MATERIALS

[76] Inventor: Byron L. Brown, 2315 Hendricks, Fort Smith, Ark. 72903

[21] Appl. No.: 441,038

[22] Filed: May 15, 1995

Related U.S. Application Data

[63] Continuation of Ser. No. 315,675, Sep. 30, 1994, abandoned, which is a continuation of Ser. No. 988,008, Dec. 9, 1992, abandoned, which is a continuation of Ser. No. 715,406, Jun. 14, 1991, abandoned.

[51] Int. Cl.$^6$ .................................................. A61B 17/56
[52] U.S. Cl. ........................................... 606/94; 606/102
[58] Field of Search .................................... 128/774, 748; 606/94, 93, 92, 86, 102; 604/100, 98, 97; 623/23, 22; 73/706, 715

[56] References Cited

U.S. PATENT DOCUMENTS

| | | | |
|---|---|---|---|
| 2,841,984 | 7/1958 | Green | 73/707 |
| 2,986,938 | 6/1961 | Grandstaff | 73/706 |
| 3,718,046 | 2/1973 | McJones | 73/395 |
| 4,226,124 | 10/1980 | Kersten | 73/706 |
| 4,357,716 | 9/1982 | Brown | 606/94 |
| 4,370,982 | 2/1983 | Reilly | 604/98 |
| 4,398,542 | 8/1983 | Cunningham et al. | 128/675 |
| 4,399,814 | 8/1983 | Pratt, Jr. et al. | 606/94 |
| 4,610,256 | 9/1986 | Wallace | 128/675 |
| 4,617,015 | 10/1986 | Foltz | 604/100 |
| 4,648,406 | 3/1987 | Miller | 128/674 |
| 4,655,749 | 4/1987 | Fischione | 604/98 |
| 4,711,233 | 12/1987 | Brown | 606/94 |
| 4,790,821 | 12/1988 | Stines | 604/98 |
| 4,858,619 | 8/1989 | Toth | 128/748 |
| 4,989,615 | 2/1991 | Hochberg | 128/774 |
| 5,009,662 | 4/1991 | Wallace et al. | 606/192 |
| 5,147,366 | 9/1992 | Arroyo et al. | 606/94 |

*Primary Examiner*—Guy V. Tucker
*Attorney, Agent, or Firm*—John L. Sigalos

[57] ABSTRACT

Method and apparatus for measuring pressures of fluid materials used in medical procedures where purity and freedom from contamination are essential. An adapter having one or more highly resilient diaphragms therein is disposed serially within a passage leading to a pressure gauge from the material whose pressure is to be measured, thereby isolating the material which is on one side of the diaphragm(s) from the volume on the other side while at the same time transmitting the pressure from the material therethrough. By carefully selecting the characteristics of the diaphragm material, the desired sensitivity of pressure conduction is achieved while maintaining the integrity of the respective volumes on both sides of the diaphragm, achieving re-usability and preventing contamination.

8 Claims, 2 Drawing Sheets

ADAPTER AND METHOD FOR MEASURING PRESSURES OF FLUID MATERIALS

This application is a continuation of application Ser. No. 08/315,675, filed Sep. 30, 1994, now abandoned, which is a continuation of application Ser. No. 07/988,008, filed Dec. 9, 1992, now abandoned which is a continuation of application Ser. No. 07/715,406, filed Jun. 14, 1991, now abandoned.

This invention relates to measuring pressures of fluids such as polymerizing plastics, and more particularly to an improved method and adapter device for use in making such measurements.

BACKGROUND OF THE INVENTION

In modern sophisticated medical procedures there is the necessity for measuring pressures of a variety of fluids. Thus in the practice of orthopedic surgery, there is the necessity for injecting polymerizing plastic materials under pressure into cavities surrounding prosthetic devices inserted within femurs so as to affix them in the desired positions. If such polymerizing plastic materials are subjected to insufficient pressure, there arises the danger of incomplete injection. On the other hand, if the pressure is excessive, there arises the danger of excessive penetration of medullary bone. Moreover, it has been found desirable to subject the injected polymerizing plastic materials to successive levels of increasing pressure; it is also desirable to delay the injection of the cement into the canal until the cement is in a moderately advanced stage of polymerization and delay the initial exposure of cement to saline, which is in blood and serum, for as long as possible. When saline is mixed with cement in the early stages of polymerization, that cement when hardened or mature will be brittle as compared with cement which was in a more advanced stage of polymerization when it first made contact with saline. Furthermore, the surface area of the cement which is initially exposed to saline should be at a minimum; minimal surface area is obtained if the cement is not driven deeply into the small medullary spaces or intertrabecular spaces. And so, if the injection of the cement into the canal is delayed until the cement is in a moderately advanced stage of polymerization (i.e., until the cement is near the dough stage), it will not penetrate intermedullary spaces. Because the use of a closed system of pressurization will be employed, the surgeon is assured that desired pressurization and penetration will be achieved.

The insertion of the prosthetic stem into the canal and cement should be a slow process so as to allow the cement in the distal end of the canal to move upward by exerting a minimum amount of pressure of less than 15 lbs/sq. inch and so the cement continues to polymerize with minimum penetration into intertrabecular spaces and with minimum surface area exposure of the cement to saline. Without a closed system of pressurization, the insertion of the prosthetic stem into the cement in the canal is done rapidly which creates a pressure of 18–20 lbs/sq inch and so the cement is driven upward toward the proximal end of the femur but is also driven laterally into the medullary spaces thereby increasing the surface area of the cement to saline at an earlier stage or less polymerized stage of the cement.

The pressures stated herein are average range of pressures which the surgeon might choose, the pressures are for the commonly used cements, namely, Howmedica's Surgical Simplex P and Zimmer's L.V.C. (low viscosity cement) for patients with systolic blood pressures of 120 mm to 150 mm of mercury. The pressures would be different for other cements; and would be different if the ratio of monomer (liquid) and polymer (powder) were to be changed.

The bleeding into the femoral canal will be stopped with 15 lbs/sq. inch if the patient's systolic blood pressure is 150 mm of mercury or stopped with 12 lbs/sq. inch if the systolic pressure is 120 mm of mercury.

When the definitive prosthetic stem with the closed system of pressuring apparatus is secured to the femur, additional cement is injected to completely fill the proximal femoral canal with a pressure of approximately 12 to 15 lbs./sq. inch which will produce hemostasis of blood for the entire cement cavity, eliminate air from the cemented area but without deep penetration of the cement into the medullary spaces. One may then delay further pressurization and allow more advanced polymerization of the cement for about one minute, then pressurize to 23 or 24 lbs./sq. inch; thereby filling the medullary spaces with a high grade of cement with minimum mixing with saline. At still approximately one minute later pressurize to 35–37 lbs./sq. inch and immediately close the inlet valve. The clearing of the cement from the inlet stem will raise the pressure 5 to 8 lbs./sq. inch with a resultant final pressure of 40–43 lbs./sq. inch.

As will be evident to one skilled in the medical arts, it is not only desirable to accurately measure and control pressure levels for the foregoing procedures, but it is also necessary to maintain integrity of the injected materials and to prevent their contamination. Moreover, since such materials solidify and become difficult to remove, it is necessary to prevent their entry into pressure measuring apparatus where they could plug up or otherwise interfere with operation.

In the past, a variety of proposals have been made to achieve the foregoing objectives. Thus, for example, cylindrical plugs often fitted out with "O" rings have been inserted into cylindrical passageways leading from the material to the gauge. Such cylindrical plugs prevent the materials from entering the gauge but have been found to be impractical with polymerizing substances. According to other proposals, a line leading from the material to the gauge has been filled with a compatible liquid. However, such a fluid filled line, with or without "O" rings permits some contamination of the material; and with polymerizing materials the line is soon plugged and the assembly becomes difficult to disassemble and service.

Still other proposals have been made in the past. Thus, transducers have been used in contact with polymerizing materials, but such transducers often require that the exposed tip of the transducer in contact with the material be covered with wax or petroleum jelly which creates a degree of objectionable contamination. Moreover, such transducers ordinarily require the connection of electrical wires leading from the material being tested to an electronic panel which receives, converts and records the impulses from the tip of the transducer insert, with the result that the equipment crowds an already busy and limited working field such as an operating table and/or room. Accordingly, there has continued to be a need for an improved pressure measuring method and apparatus.

BRIEF SUMMARY OF THE INVENTION

The improvements according to the invention, provides an air-tight seal between a pressure gauge and the material whose pressure is to be measured. Within a line leading to the pressure measuring device, there is inserted an adapter fitted with a resilient diaphragm which isolates the space on one side thereof from the space on the other side thereof while communicating changes in pressure on one side of the diaphragm to the remainder of the line on the other side. Where polymerizing materials are employed, a core of the material develops and extends into the diaphragm. Since the diaphragm is very resilient, it distends under pressure so as to reduce the volume of space on the downstream (i.e., pressure gauge) side; and since the downstream volume is confined, the pressure of the gas or liquid therein is correspondingly changed thus imparting to the pressure gauge a corresponding pressure change that then is measured and displayed.

By selecting a preferred type of material from which the diaphragm is made, its characteristics provide a high degree of resiliency and pressure transmission while ensuring isolation, preventing contamination, and retaining the qualities of cleanability so as to make the adapter readily re-usable.

Further, in accordance with the preferred embodiment, the adapter is made to be geometrically cylindrical and is fitted with threaded portions adapted for insertion in conventional lines, thus facilitating compatibility and use in with conventional equipment.

OBJECTS AND FEATURES OF THE INVENTION

It is one general object of the invention to improve equipment for measuring pressures of fluid materials utilized in medical procedures.

It is another object of this invention to facilitate cleaning and re-use of equipment for measuring pressures of fluid materials utilized in medical procedures.

It is yet another object of this invention to prevent contamination of pressure sensing medical equipment.

It is still another object of the invention to prevent damage to pressure transducers used in sensing the pressure of fluid materials utilized in medical procedures.

Accordingly, in accordance with one feature of the invention, an adapter is serially inserted within a line leading from a reservoir of pressurizable fluid materials to a pressure transducer, the adapter including an isolator to prevent flow of the fluid therethrough while transmitting an indicia of pressure, thereby isolating the fluid from the pressure transducer.

In accordance with another feature of the invention, the isolator comprises a resilient impenetrable diaphragm which expands and contracts in response to increases and decreases in pressure of the pressurizable fluid materials, thereby changing the volume within a predetermined space on the opposite side of the diaphragm from the fluid materials diaphragm and correspondingly changing the pressure within such predetermined space.

In accordance with yet another feature of the invention, the aforementioned predetermined space is interconnected with a conventional pressure transducer such as a pressure gauge, thereby effectively isolating the gauge from the pressurizable fluid materials while at the same time causing the gauge to assume a position indicative of the pressure of the such pressurizable fluid materials.

In accordance with still another feature of the invention, the aforementioned predetermined space can be charged with either gas or liquid, thus enhancing the versatility of the adapter.

In accordance with another feature of the invention, according to a preferred embodiment, the aforementioned resilient diaphragm is constructed of materials which are compatible with pressurizable fluid materials often encountered in conducting medical procedures, thus enhancing attractiveness of the adapter.

In accordance with yet another feature of the invention, in one preferred embodiment, the diaphragm is made of latex (rubber), a material that is unaffected by solvents used to remove fluid or congealed fluid substances such as the polymerizing plastics often used in cementing prostheses within femoral canals, thus facilitating cleansing, sterilization and re-use of the adapters.

These and other objects and features of the invention will become apparent from the following detailed description, by way of preferred examples, with reference to the drawings.

DESCRIPTION OF A PREFERRED EMBODIMENT

Figure 1:
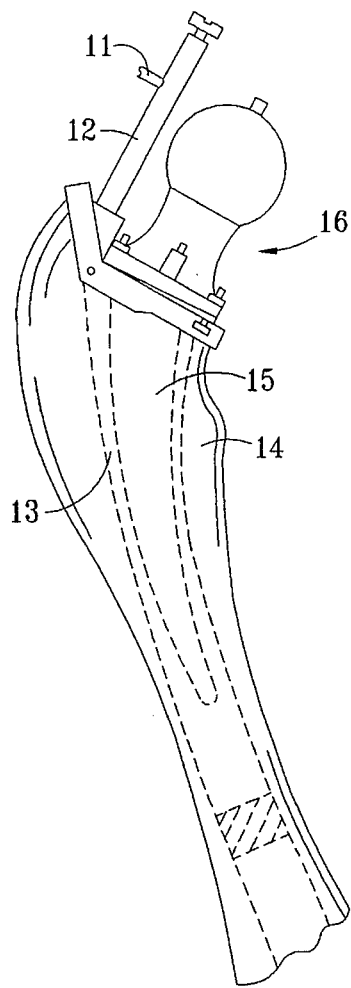
FIG. 1 is a perspective view of certain equipment illustrative of the prior act.

Now turning to the drawing, and more particularly FIG. 1 thereof, it will be observed that it depicts a femur and a prostheses positioning device as illustrated in U.S. Pat. No. 4,357,716 the description of which is incorporated herein by reference. As will be evident from reference to that patent as well as others (e.g., U.S. Pat. No. 4,711,233), there often arise occasions when in the practice of orthopedic surgery, it becomes necessary or desirable to inject cementing fluids into cavities under controlled pressure.

As described in connection with FIG. 5D of U.S. Pat. No. 4,357,716, a suitable polymerizing plastic fluid material such as methyl methacrylate cement is inserted through inlet 11 from a suitable source (not shown in FIG. 1) and flows downwardly through hollow stem and connecting passageways into the space 13 between the walls of femur 14 and the prosthetic stem 15 and the lower part of the prosthetic device 16. As mentioned above, if such cementing materials are subjected to insufficient pressure, there arises the danger of incomplete injection. On the other hand, if the pressure is excessive, there arises the danger of excessive penetration of medullary bone. Moreover, it has been found desirable to subject the injected polymerizing plastic materials to successive levels of increasing pressure: for example, initial pressures up to 15 psi which create hemostasis of blood or bleeding into the medullary spaces, eliminates air and is thought to drive some blood back into vascular channels; next, after a brief period (e.g., one to three minutes) to permit an increase in viscosity, an increase in pressure to the 23–24 lbs./sq. inch range; and, depending upon the characteristics of the polymerizable materials employed, a possible third stage in which the pressure is increased to a level lying in the range of from 40 to 45 psi. Accordingly, as schematically illustrated in FIG. 2, a pressure monitoring and control system is employed.

Figure 2:
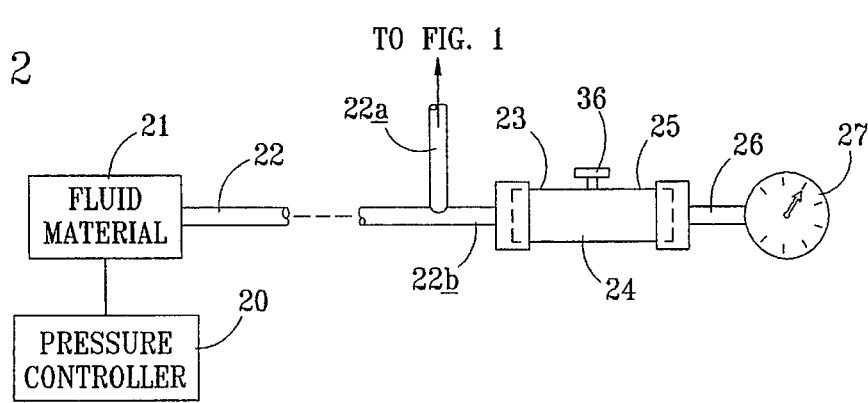
FIG. 2 is a schematic view illustrating the principal components of a system embodying the adapter according to the invention hereof.

Now turning to FIG. 2, there is depicted a simple system illustrating the practice of the invention. There, it will be observed is shown a conventional pressure controller 20, which is connected to and controls pressure of the fluid materials 21. Materials 21 are conducted through any suitable means such as conventional tubing sections 22 and 23 to an intake orifice such as orifice 11 in FIG. 1.

In order to provide an indication of the pressure to which fluid materials 21 are subjected, an extension of tubing 22 is provided and identified as extension 22b. This extension 22b is in fluid-communicating relationship with the principal portions 22 and 22a through which the fluid materials 21 flow to the point of use. Thus, the input end 23 of adapter 24 is in fluid communication with the fluid materials 21.

Also as shown in FIG. 2, the output end 25 of adapter 24 is connected through a suitable intermediary such as tubing 26 to a pressure transducer 27 which is illustrated as a conventional dial-type pressure gauge. Although the pressure transducer is thus shown, it will be evident to one skilled in the art that other types of transducers could be employed in practicing the principles of the invention. Thus, for example, any one of a number of known electronic transducers such as those with digital readouts could be employed. Since, for the reasons set forth above, it is necessary that the fluid materials 21 be constrained from contacting the gauge 27, there is provided within adapter 24 an isolating resilient diaphragm 30 as shown in FIGS. 3 and 4.

Figure 3:
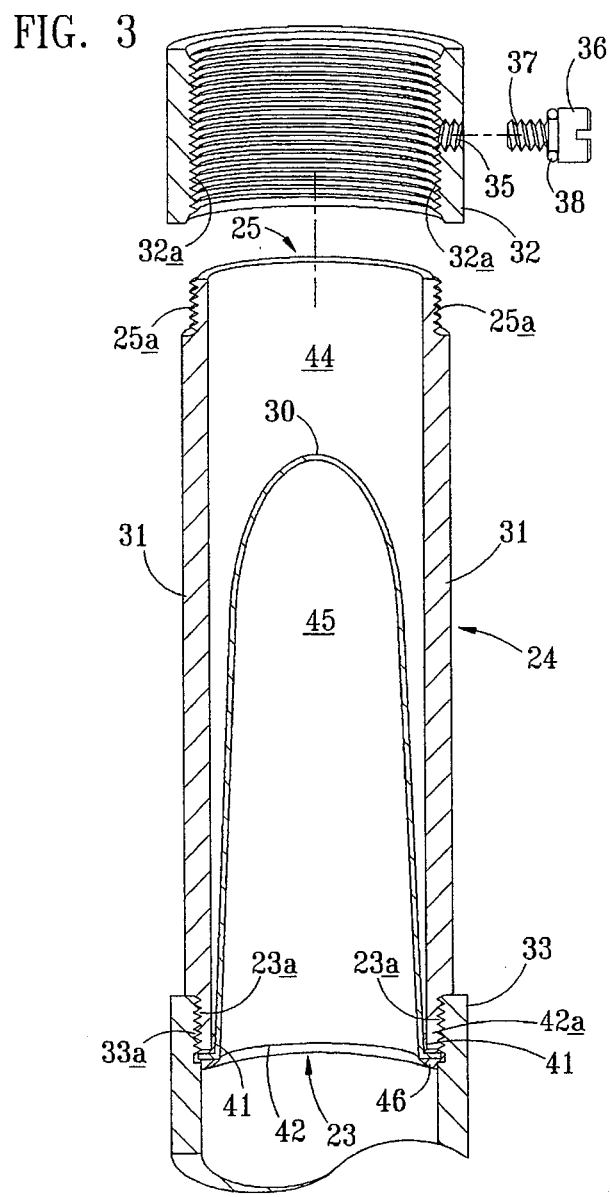
FIG. 3 is a hemi-sectional view of the adapter according to the invention illustrating a removable coupling and showing the interior isolating diaphragm in an extended condition.

Now turning to FIG. 3, it will be observed that it depicts the adapter 24 in hemi-sectional form. In its preferred form, the adapter 24 is cylindrical in shape (as shown), and representations of FIGS. 3 and 4 is made hemi-sectional in order to most clearly portray its essential components and geometries. However, it will be evident to one skilled in the art that its cross-sectional shape could be other than circular without departing from the principles hereof. Thus, for example, its cross-sectional shape could be oval or elliptical.

Figure 4:
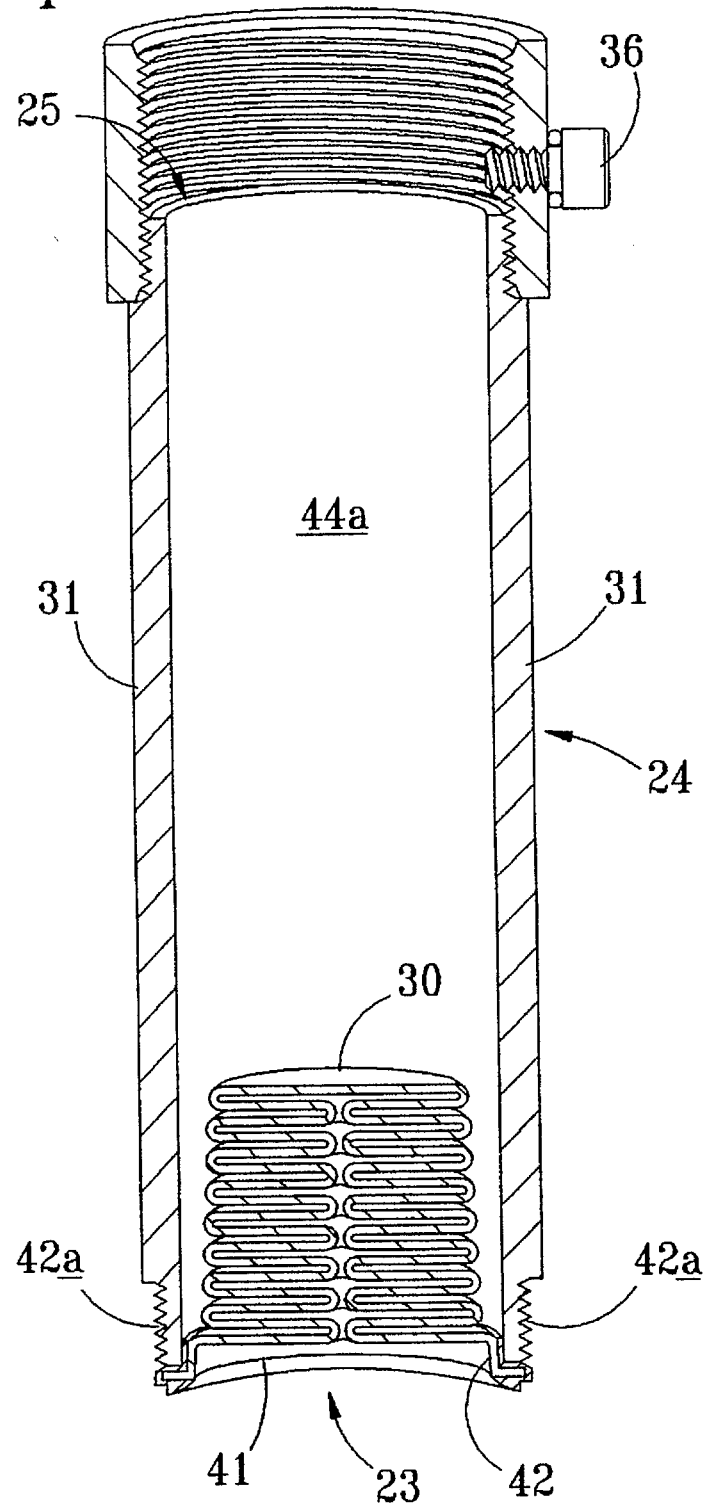
FIG. 4 is a hemi-sectional view of the adapter according to the invention showing the interior isolating diaphragm in a contracted condition.

The views of FIGS. 3 and 4 is that of the adapter after having been cut vertically in a plane passing through the center line of the adapter, and thus, the figures show the rear 180 degree segment of the adapter 24.

As mentioned above, FIG. 3 shows the adapter with diaphragm 30 in its extended position. The adapter 24 in its preferred form comprises cylindrical housing 31 fitted at the output end 25 with threads 25a adapted for engagement with a mating fitting 32 and at the input end 23 with threads 23a adapted for engagement with a mating fitting 33. Fittings 32 and 33 are included to provide a means of coupling with interconnecting tubing such as tubing 22 and 26 (FIG. 2). However, it will be evident to one skilled in the art that other types of fittings or connectors could be employed to couple adapter 24 into the system.

At least a part of the interior surface of fitting 32 is threaded with threads 32a so as to engage mating threads 25a; and at least a part of the interior surface of fitting 33 is threaded with threads 33a so as to engage mating threads 23a.

As shown in FIG. 3, there is provided within fitting 32, a threaded aperture 35 which is adapted for receiving and securing pressure release plug 36. As will be observed, plug 36 is fitted with mating threads 37 for engagement with corresponding threads of threaded aperture 35; and in order to provide an effective seal, with one or more "O" rings represented by symbol 38.

Isolating resilient diaphragm 30 can be made of any of a variety of suitable materials having the desired qualities of resiliency, durability, compatibility, cleanability and impervious to passage therethrough of the materials whose pressure is to be monitored. However, in accordance with the preferred embodiment, the most desirable material that has thus far been found suitable for use when using cements such as methyl methacrylate cement is thin latex rubber balloon, which at rest or when not inflated has a diameter which is at least 1 millimeter less than the inside diameter of the cylinder of the adaptor 24.

Further reference to FIGS. 3 and 4 will reveal that the base 40 of diaphragm 30 is affixed and sealed as at 41 to the lower part of the interior walls of cylindrical housing 31 so as to prevent flow therethrough. Such sealing can be accomplished by any of a variety of known techniques. However, it has been found preferable to employ a bonding material such as (cyanoacrylate ester) Super-glue to fix the diaphragm to the cylinder; and to coat the lower surface 42 of diaphragm 30 together with the adjacent surfaces 42a of the interior housing 31 with a silicone elastomer such as Silastic cement 46. The end portions of diaphragm 30 may be turned around the end surfaces of the adapter housing, (as shown), or they may be affixed in any of a variety of ways known to those skilled in the art. The sealing material is then allowed to set or cure so as to harden and provide the aforementioned seal 41.

Since the material from which diaphragm 30 is made is impervious to the aforementioned fluid cementing materials, it will be evident that once seal 41 is completed, diaphragm 30 effectively isolates the volumes on either side of it from the other. Thus, the volumes represented by numerals 44 and 45 are effectively isolated one from the other. However, an indicia of pressure existing within volume 45 can be communicated through diaphragm 30 and volume 44 as is described hereinafter.

If a pressure transducer is connected in communication with volume 44 as, for example, illustrated in FIG. 2, and if pressure plug 36 is tightened in place, then the volume represented by symbol 44 and the interconnected volume of tubing 26 (FIG. 2) is finite and will vary in inverse proportion to the degree to which diaphragm 30 extends thereinto. Thus, when diaphragm 30 is in its retracted or collapsed condition as shown in FIG. 4, the volume 44a residing above it is greater than the corresponding volume 44 when the diaphragm is extended as shown in FIG. 3.

When in use with pressures lying in the range for which it is designed, the adapter 24 is connected as schematically shown in FIG. 2. Accordingly, when pressure is increased in the input end 23, there results a corresponding movement of diaphragm 30 into a portion of volume 44a, thereby correspondingly increasing the pressure therein. Such pressure is communicated to the pressure transducer (e.g., gauge 27 of FIG. 2).

FIGS. 3 and 4 illustrate the principles of the invention when volume 44/44a is confined and when such volume is filled with either a compressible gas or compressible fluid, or if gauge 27 in effect provides the equivalent of compressibility. Otherwise, if volume 44/44a is filled with an essentially incompressible substance such as water, pressure on the input end of adapter 24 would be transmitted through diaphragm 30 without appreciable movement thereof.

In the preferred embodiment, the pressure transducer (as represented by gauge 27) includes the characteristic that the fluid volume therein varies as a function of pressure, thereby in effect simulating the characteristic of fluid compressibility and permitting diaphragm 30 to move from a retracted position as shown in FIG. 4 to an extended position as shown in FIG. 3. Accordingly, an essentially incompressible fluid or semi-compressible fluid can be employed, and the preferred type of fluid for use has been found to be glycerins. Sterile water may be used but is more corrosive to the gauge than glycerine.

To facilitate the desired functioning of the diaphragm 30, a plunger may be employed on the upstream side, the downstream side or both to position the balloon in a collapsed position before filling the adaptor with fluid (glycerins). If thus employed, the plunger takes the shape of a movable plug of material that moves with pressure and corresponding shape of diaphragm 30. In such event, the cross section of the plunger should be less than the corresponding internal dimension of the adapter so as to permit freedom of movement therebetween.

It has been found preferable also for the adapter housing to be constructed of clear material so as to facilitate viewing of the condition of the diaphragm 30, thus providing a way of avoiding development of excess pressure beyond that for which the Although the invention hereof has been described by way of example of a preferred embodiment, it will be evident that other adaptations and modifications can be employed without departing from the spirit and scope thereof. For example, a pair of diaphragms could be positioned in tandem within the adapter, and an essentially non-compressible fluid disposed therebetween, thereby providing enhanced protection against contamination.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. Apparatus for measuring pressures of uncontaminated medical polymerizing materials while maintaining the uncontaminated state of such fluid materials comprising:

(a) a source of said uncontaminated medical polymerizing materials having a communicating orifice therein for communicating said fluid materials therewithin;

(b) an adapter having a pair of opposed ends, and an internal passageway extending therethrough, from one end to the other end;

(c) means for interconnecting said one end of said adapter with said communicating orifice, thereby to expose said one of said ends to said uncontaminated medical fluid materials;

(d) an inflatable and expandable diaphragm means having an inner surface and an outer surface, said diaphragm means being affixed within said adapter for contacting said polymerizing materials with said inner surface, for preventing said polymerizing materials from traversing said internal passageway, and for defining a variable volume within said adapter, extending from said outer surface to said other end; and (e) pressure measuring means connected to said other end and closing said other end, thereby to enclose said variable volume, said pressure measuring means measuring pressure within said variable volume.

2. Apparatus according to claim 1 in which said pressure measuring means includes a pressure display device.

3. Apparatus according to claim 1 in which at least a portion of said adapter is transparent.

4. An adapter system for measuring pressure of polymerizing material, comprising:

(a) a source of polymerizing material;

(b) an orthopedic prosthetic device-positioning member having a communication orifice;

(c) an elongated tubular member having a pair of opposed ends and an internal passageway extending therethrough, from one end to the other end;

(d) means for interconnecting said one end of said tubular member with said source of polymerizing material and with said communicating orifice of said orthopedic prosthetic device-positioning member, thereby exposing said one end of said elongated tubular member to said polymerizing material;

(e) inflatable and expandable diaphragm means having an inner surface and an outer surface, said diaphragm means being affixed within said tubular member for contacting said polymerizing materials with said inner surface, for preventing said polymerizing materials from traversing said internal passageway, and for defining a variable volume, dependent upon the pressure presented by said polymerizing material, within said tubular member extending from said outer surface to said other end; and (f) a pressure transducer connected to said other end and closing said other end thereby to enclose said variable volume, said pressure transducer measuring pressure within said variable volume.

5. An adapter system according to claim 4 in which at least a portion of said elongated tubular member is transparent.

6. An adapter system according to claim 4 in which said pressure transducer is a pressure gauge.

7. An adapter system according to claim 6 in which at least a portion of said elongated tubular member is transparent.

8. A method of measuring and displaying pressure of a polymerizing material used in medical procedures comprising;

(a) providing a source of said polymerizing material;

(b) providing a communicating orifice for said source of said polymerizing material thereby providing access to said source of said first fluid material;

(c) interconnecting an enclosed channel with said orifice;

(d) disposing within said enclosed channel an inflatable and expandable resilient diaphragm to block passage through said enclosed channel of said first fluid material to define a first variable volume for said polymerizing material on the first fluid side of said diaphragm, and a second discrete volume on the other side of said diaphragm;

(e) disposing within said second discrete volume a second fluid material;

(f) applying pressure to said polymerizing material thereby causing said polymerizing material to enter said expandable resilient diaphragm, reducing the volume of said second discreet volume, and transmitting said pressure of said polymerizing material therethrough to said second fluid material while preventing migration of said fluid materials between said first and said second fluid materials: and (g) measuring the pressure of said second fluid material.

* * * * *